US008870797B2

(12) United States Patent
Paradis (10) Patent No.: US 8,870,797 B2
(45) Date of Patent: *Oct. 28, 2014

(54) NON-INVASIVE DEVICE FOR SYNCHRONIZING CHEST COMPRESSION AND VENTILATION PARAMETERS TO RESIDUAL MYOCARDIAL ACTIVITY DURING CARDIOPULMONARY RESUSCITATION

(76) Inventor: Norman A. Paradis, San Marcos, CA (US)

( * ) Notice: Subject to any disclaimer, the term of this patent is extended or adjusted under 35 U.S.C. 154(b) by 1070 days.

This patent is subject to a terminal disclaimer.

(21) Appl. No.: 12/685,289

(22) Filed: Jan. 11, 2010

(65) Prior Publication Data

US 2010/0114220 A1    May 6, 2010

Related U.S. Application Data

(62) Division of application No. 10/973,775, filed on Oct. 25, 2004, now Pat. No. 7,645,247.

(51) Int. Cl.
| | | |
|---|---|---|
| A61H 19/00 | (2006.01) | |
| A61H 31/02 | (2006.01) | |
| A61B 5/02 | (2006.01) | |
| A61M 16/00 | (2006.01) | |
| A61H 31/00 | (2006.01) | |

(52) U.S. Cl.
CPC ........ *A61H 31/005* (2013.01); *A61H 2031/001* (2013.01); *A61M 16/00* (2013.01); *A61H 2201/5007* (2013.01); *A61H 31/007* (2013.01); *A61H 31/006* (2013.01); *A61H 2230/04* (2013.01); *A61H 2201/5048* (2013.01); *A61H 2201/5058* (2013.01); *A61M 2205/332* (2013.01)
USPC ............. 601/152; 601/151; 601/149; 601/44; 600/508

(58) Field of Classification Search
CPC ....... A61H 9/00; A61H 9/0007; A61H 9/005; A61H 9/0078; A61H 23/04; A61H 31/00–31/007; A61M 1/10; A61M 1/1005; A61M 1/1037; A61M 1/106; A61B 5/026; A61B 5/0261; A61B 5/0295; A61B 5/02; A61B 5/0205; A61B 8/06
USPC ........... 601/1, 15, 41–44, 107, 108, 148–152, 601/DIG. 9; 607/3, 5–7
See application file for complete search history.

(56) References Cited

U.S. PATENT DOCUMENTS

| | | | | |
|---|---|---|---|---|
| 4,198,963 | A | * | 4/1980 | Barkalow et al. ............. 601/106 |
| 4,273,114 | A | | 6/1981 | Barkalow et al. |

(Continued)

OTHER PUBLICATIONS

Asthon et al., "Effect of rescuer fatigue on performance of continuous external chest compressions over 3 min", Resuscitation, Nov. 2002;55(2):151-5.

(Continued)

*Primary Examiner* — Rachel Young
(74) *Attorney, Agent, or Firm* — Nixon & Vanderhye P.C.

(57) ABSTRACT

A method for improving the cardiac output of a patient who is suffering from pulseless electrical activity or shock and yet still displays some myocardial wall motion including sensing myocardial activity to determine the presence of residual left ventricular pump function having a contraction or ejection phase and a filling or relaxation phase. In such cases, a compressive force is repeatedly applied to the chest based on the sensed myocardial activity such that the compressive force is applied during at least some of the ejection phases and is ceased during at least some of the relaxation phases to permit residual cardiac filling, thereby enhancing cardiac output and organ perfusion. Also incorporated may be a logic circuit capable of utilizing multiple sensing modalities and optimizing the synchronization pattern between multiple phasic therapeutic modalities and myocardial residual mechanical function.

86 Claims, 3 Drawing Sheets

(56) References Cited

U.S. PATENT DOCUMENTS

| | | | |
|---|---|---|---|
| 4,928,674 A | 5/1990 | Halperin | |
| 5,020,516 A * | 6/1991 | Biondi et al. | 601/44 |
| 5,490,820 A * | 2/1996 | Schock et al. | 601/41 |
| 5,496,257 A * | 3/1996 | Kelly | 601/41 |
| 5,496,351 A | 3/1996 | Plicchi et al. | |
| 6,053,869 A * | 4/2000 | Kawagishi et al. | 600/443 |
| 6,179,793 B1 | 1/2001 | Rothman et al. | |
| 6,234,985 B1 * | 5/2001 | Lurie et al. | 601/41 |
| 6,298,267 B1 * | 10/2001 | Rosborough et al. | 607/6 |
| 6,351,671 B1 | 2/2002 | Myklebust et al. | |
| 6,480,733 B1 | 11/2002 | Turcott | |
| 6,620,116 B2 * | 9/2003 | Lewis | 601/41 |
| 6,752,771 B2 * | 6/2004 | Rothman et al. | 601/44 |
| 7,220,235 B2 * | 5/2007 | Geheb et al. | 601/41 |
| 7,645,247 B2 * | 1/2010 | Paradis | 601/41 |
| 2001/0027279 A1 | 10/2001 | Rothman et al. | |
| 2004/0039313 A1 * | 2/2004 | Sherman et al. | 601/21 |
| 2004/0116969 A1 | 6/2004 | Owen et al. | |
| 2004/0230140 A1 | 11/2004 | Steen | |
| 2005/0080363 A1 * | 4/2005 | Jensen et al. | 601/44 |
| 2005/0256415 A1 * | 11/2005 | Tan et al. | 600/509 |
| 2006/0100556 A1 * | 5/2006 | Hargens et al. | 601/11 |
| 2006/0190045 A1 | 8/2006 | Marcus et al. | |
| 2007/0060785 A1 | 3/2007 | Freeman et al. | |
| 2008/0082135 A1 | 4/2008 | Arcot-Krishnamurthy et al. | |
| 2008/0161894 A1 | 7/2008 | Ben-David et al. | |

OTHER PUBLICATIONS

Bayly et al., "Synchronous versus nonsynchronous high-frequency jet ventilation: effects on cardiorespiratory variables and airway pressure in postoperative patients", Crit Care Med. Oct. 1987; 15(10):915-7.

Bendjelld et al., Correlation between measured inferior vena cava diameter and right atrial pressur depends on the echocardiographic method used in patients who are mechanically ventilated, J Am Soc Echocardiogr, Sep. 2002; 15(9):944-9.

Bocka et al., Electromechanical Dissciation in Human Beings: An Echocardiographic Evaluation, Annals of Emergency Medicine, May 1988, p. 450-452.

Boese et al., "Optomizing temporal resolution in CT with retrospective ECG gating", Radiologe, Feb. 2000;40(2):123-9.

Bottiger et al., Emergency medicine—new concepts and therapies improve outcome from cardiac arrest, Anasthesiol Intensivmed Notfallmed Schmerzlyer. Jan. 2003; 38(1):63-7.

Bradley et al., "Blood flow; magnetic resonance Imaging", Radiology, Feb. 1985; 154(2):443-50.

Cobb et al., "Changing incidence of out-of-hospital ventricular fibrillation, 1980-2000", JAMA, Dec. 2002 18(288(23):3008-13.

Counselman et al., "The status of bedside ultrasonography training in emergency medicine residency programs", Acad Emerg Med. Jan. 2003; 10(1):37-42.

Etiology, Electrophysiology, and Myocardial Mechanics of Pulseless Electrical Activity, Ture and Psedo-Pulseless Electrical Activity, p. 331-332, 1989, 1992.

Gebber GL, "Basis for phase relations between baroreceptor and sympathetic nervous discharge", Am J Physiol, Feb. 1976; 230(2): 263-70.

Hayes et al., "Monitoring during cardiac arrest: are we there yet?", Curr Opin Crit Care., Jun. 2003; 9(3): 211-7.

Lanzer et al., "ECG-synchronized cardiac MR imaging: method and evaluation", Radiology. Jun. 1985; 155(3):;681-6.

Lanzer et al., "Cardiac imaging using gated magnetic resonance", Radiology. Jan. 1984; 150(1)0;121-7.

Linder et al., "New mechanical methods for cardipulmonary resuscitation (CPR). Literature study and analysis of effectiveness", Anaesthesist, Mar. 1997;46(3):220-30.

Liu et al., "An efficient MR phosphorus spectroscopic localization technique for studying ischemic heart", J Magn Reson Imaging. Nov. 1999; 10(5):892-8.

Lorusso et al., Hemodynamic effects in acute cardiomyoplasty of different wrapped muscle activation times as measured by pressure-volume relation, J Card Surg. May-Jun. 1996;11(3):217-25.

Marek et al., "Correction of morphology and indicators of atrial function using long-term physiologic cardiac pacing in patients with prior chronic atrioventricular dissociation or VVI pacing", Vnitr Lek. Sep. 1999;p. 45(9):513-7.

Modersohn et al., "Diastolic heart function—pathophysiology, characterization, and therapeutic approaches", Clin Cardiol. Dec. 1993; 16(12):850-8.

Morris-Thurgood et al., "Pacing in heart failure: improved ventricular interaction in diastole rather than systolic re-synchronization", Europace, Oct. 2000;2(4):271-5; duscussion 276.

Ordonez et al., "Assessment of the effectiveness of descending aortomyoplasty for nonischemic cardiac failure by means of the subendocardial viability index", Ann Thorac Cardiovasc Surg. Feb. 2001:7(1):17-22.

Paradis et al., "Aortic Pressure during Human Cardia Arrest: Identification of Psedo-Etectromechanical Dissociation", Chest, Jan. 1992, pp. 123-128.

Parish et al., "Success changes the problem:why ventricular fibrillation is decling, why pulseless electrical activity is emerging, and what to do about it", Resuscitation, Jul. 2003; 58(1): 31-5.

Rudiger, A et al., "Frequency and outcome of in-hospital resuscitation outside the ICU-setting", Swiss Med Wkly., Jan. 24, 2004; 134(3-4):59-62.

Thornton et al.,"Dynamic stiffness and implications for assisting the operation of the left ventricle", IMA J Math Appl Med Biol. Dec. 1996; 13(4):275-95.

Tortoli et al., Toward a better quantitative Measurement of Aortic Flow, Elsevier, Ultrasound in Med & Biol vol. 28, No. 2, pp. 249-257, 2002.

Veenstra et al., "Electrotonic interactions between aggregates of chick embryo cardiac pacemaker cells", Am J Physiol. Mar. 1986; 250(3 Pt 2):H453-63.

Vinet et al., "Analysis of an iterative difference equation model of the cardiac cell membrane", J Theor Biol. Sep. 21, 1994; 170(2):201-14.

Vural et al., "Optimization of synchronization delay in latissimus dorsi dynamic cardiomyoplasty", Ann Thorac Surg. May 1998;65(5)1231-4.

Wenzel, Drug theraphy in cardiopulmonary resuscitation, Wien Klin Wochenschr, Dec. 17, 2001;113(23-24):915-26.

* cited by examiner

NON-INVASIVE DEVICE FOR SYNCHRONIZING CHEST COMPRESSION AND VENTILATION PARAMETERS TO RESIDUAL MYOCARDIAL ACTIVITY DURING CARDIOPULMONARY RESUSCITATION

RELATED APPLICATION

This application is a divisional application of U.S. patent application Ser. No. 10/973,775 filed Oct. 25, 2004, (U.S. Pat. No. 7,645,247), the entirety of which is incorporated by reference.

BACKGROUND OF THE INVENTION

This invention relates generally to the field of cardiovascular medicine, and in particular to the treatment of patients suffering from a spectrum of cardiac states, ranging from shock to pulseless electrical activity, in which the patient appears to be lifeless and in cardiac arrest yet retains some mechanical activity in the myocardial wall motion.

One common technique for treating persons suffering from cardiac arrest is the use of cardiopulmonary resuscitation or CPR. In this procedure, the patient's chest is repeatedly compressed, often in combination with periodic ventilations. Administration of electrical countershock and drugs intended to assist in restoration of cardiopulmonary function to chest compression and ventilation, constitutes advanced life support.

For a variety of reasons, the effectiveness of CPR has been limited. Hence, devices or techniques which can improve the effectiveness of CPR are greatly needed.

In additional to sudden cardiac arrest, refractory-shock is often fatal. For example, if not properly stabilized, a person suffering from shock can progress into cardiac arrest, which, because it is not sudden in nature, is invariably fatal. Emergency medicine and critical care practitioners approach the treatment of shock principally by attempting to alleviate the cause, although there are no non-invasive techniques that may beneficial in assisting circulation. Hence, devices and techniques are also needed to treat those suffering from refractory shock and shock that is progressing toward cardiac arrest.

There is no general consensus as to when is the appropriate time to start administering CPR as the patient's blood pressure progressively decreases. This relates to concern that chest compression may interfere with residual cardiac function, even though CPR may at some point be beneficial in shock patients as they progress to cardiac arrest. Hence there a need for a device or technique to prevent CPR from interfering with residual cardiac function.

Unlike ventricular fibrillation—PEA is a heterogeneous entity with respect to cardiac function and hemodynamics. Various studies have documented that between 40-88% of patients with PEA had residual cardiac mechanical activity. In this condition of pseudo-PEA, the patient may appear lifeless and without a pulse, despite some degree of residual left ventricle function and hemodynamics. The outcome of patients suffering PEA has tended to be worse than those in ventricular fibrillation, possibly reflecting the potential of CPR and residual myocardial mechanical activity to interfere with each other's efficacy. Hence there is a need for a device or technique to enhance the efficacy of CPR in PEA.

BRIEF DESCRIPTION OF THE INVENTION

The invention provides various techniques and systems for treating those suffering from a variety of pathophysiologic states ranging from refractory shock to those who appear to be lifeless, yet who still retain some degree of residual myocardial mechanical function. It has been observed when performing open chest cardiac massage, that coordinating compression and relaxation with the heart's residual mechanical activity improves recovery of cardiac function. Extrapolating from this, if mechanical myocardial function is present but inadequate, as in PEA, external chest compressions should be directed toward assisting ejection—that is compressing the chest during its intrinsic contractions—and then releasing the chest so as not to interfere with ventricular filling. CPR that is not synchronized with the heart's residual mechanical function may result in application of the compression phase when the left ventricle is trying to fill, resulting in significantly decreased cardiac output on the next ejection secondary to Frank-Starling Law. Interference with ventricular filling by compression of the chest can be so deleterious that it can, in and of itself, cause complete loss of residual myocardial function resulting in true cardiac arrest.

Once a system has been designed to detect residual myocardial activity in apparently lifeless patients, the system can output not only to chest compression devices but to any intervention found to benefit from synchronization, including but not limited to: abdominal counter-pulsation, ventilation, phasic limb-compression, myocardial electrical stimulation, intravascular fluid shifting, intravascular balloon inflation-deflation, intra-esophageal or intra-pericardial balloon inflation, application of transthoracic electromagnetic irradiation, and the like.

In one specific embodiment, the invention provides a method for improving the cardiac output of a patient who is suffering from pulseless electrical activity or shock and yet still displays some myocardial wall mechanical activity. According to the method, myocardial activity is sensed to determine the presence of residual ventricular phasic movement with or without residual left or right ventricular pump function having an ejection phase and a relaxation phase. A compressive force is repeatedly applied to the heart based on the sensed myocardial activity such that the compressive force is applied during at least some of the ejection phases and is ceased during at least some of the relaxation phases to permit residual cardiac filling, thereby creating or enhancing cardiac output and organ perfusion. This synchronization process can also be used when the patient's chest is actively lifted during decompression. In this way, the chances for improving the outcome of patients suffering from shock or cardiac arrest are improved.

The compressive force may be applied over a wide and potentially variable range of time intervals. For example, the compressive force may be applied for only a certain portion of the contraction or ejection phase, such as at the beginning, middle or end. As another example, the compressive force may be applied during each and every sensed contraction or ejection phase, or only at certain contraction or ejection phases. In other words, the start of the compression and the duration of the compression can be adjusted to improve outcomes.

In one option, ventilations may be applied based on the sensed myocardial activity. This may be done manually, or using a mechanical ventilator, or the like.

In another aspect, the compressive force may be applied using a variety of devices or equipment. Some examples include mechanical chest compression devices, inflatable vests, nerve stimulators, abdominal compression devices, chest or abdominal active decompression devices, limb phasic compression devices, and the like. Further, the compressive force may be applied at different locations on the chest, abdomen, limbs, or back, such as the left lateral chest, point of maximal impulse and the like.

In a further aspect, the myocardial activity may be sensed using a variety of sensing systems. Such systems may include electrocardiography, Doppler ultrasonography, plethysmography, phonocardiography, echocardiography, transthoracic impedance and the like. These may be incorporated into a probe that is coupled to the chest, abdomen, back, extremities, or a combination of these, or placed within the body, such as within the esophagus, trachea, or stomach.

In some cases, chest compressions may be performed manually, such as using traditional CPR techniques. In such cases, an audio and/or visual signal may be produced to indicate when the ejection phase is sensed. In this way, the rescuer will be prompted as to when to apply the compressive force. The tone or volume of the synchronizing prompt may be varied so as to assist the rescuer in providing optimal CPR. In some cases, the chest, abdomen, or extremities may also be actively or passively compressed or decompressed in an alternating manner with chest compressions, and in synchronization with either cardiac ejection or filling. The starting point and length of compression or decompression can also be adjusted to improve outcomes.

In another embodiment, the invention further provides a system for improving the cardiac output of a patient who is suffering from pulseless electrical activity or shock and yet still displays some myocardial wall motion. The system comprises a myocardial activity sensor that is adapted to sense movement of the myocardial wall and or myocardial valvular motion to determine the presence of residual left ventricular contract and relaxation, and/or pump function having an ejection phase and a filling phase. The system may also include a compression device that is configured to repeatedly apply a compressive force to the heart, either through the chest wall, intrathoracically through the pericardium, or directly to the myocardium through a endoscope and pericardial window. Further, a controller is employed to receive signals from the myocardial activity sensor and to control operation of the compression device such that the compression device repeatedly applies a compressive force to the heart such that the compressive force is applied during at least some of the ejection phases and is ceased during at least some of the relaxation phases to permit residual cardiac filling, thereby enhancing cardiac output and organ perfusion.

As an option to using a compression device, chest compressions may be performed manually. In such cases, the system may include a cadence device that is configured to produce audio and/or visual signals indicative of when compressive forces to the heart are to be applied and ceased. This same cadence system may be utilized to synchronization other therapies such as ventilation or abdominal counterpulsation.

The myocardial activity sensors that may be used include electrocardiography sensors, Doppler ultrasonography sensors, plethysmography sensors, phonocardiography sensors, echocardiography sensors Transthoracic impedance sensors, magnetic resonance imaging, and radiographic fluoroscopy. These sensors may be placed on the patient's chest, abdomen, back or extremities, within body cavities such as the esophagus, or some distance from the patient in the case of technologies like radiography or magnetic resonance imaging. If the patient has an arterial pressure catheter in place, the controller may also utilize that signal for synchronization. Further, the controller may be configured to apply the compressive force during each sensed ejection phase or during only at certain ejection phases. As another option, the controller may be configured to apply the compressive force for only a certain duration of the ejection phase.

The system may further include a ventilator device that is configured to provide ventilation to the patient based on the sensed myocardial activity. The controller may also vary the pattern of individual ventilations so as to optimize synchronization.

In one particular aspect, the compression device may be a mechanical compression device, an inflatable vest, a nerve stimulator, or the like. Further, the system may include a lifting device that is configured to actively decompressing the chest during the relaxation phase, or compress the abdomen during chest decompression.

In another embodiment, the invention incorporated a logic circuit capable of varying the therapeutic device or devices such that the optimal pattern and combination of synchronization, force, and vector can be determined and applied. This pattern may be variable over time and the invention will monitor for the possibility by occasionally varying the pattern of therapies and adjusting accordingly. In the latter case, an input that correlates with cardiac output, such as exhaled end-tidal carbon dioxide or vital organ oxymetry may be utilized as the indicator of blood flow.

During resuscitation of patients suffering cardiac arrest, the presence and degree of residual left ventricular mechanical activity may vary over time. The invention may be configured to detect transient periods of left ventricular mechanical activity and attempt synchronize therapies during the periods so as to assist residual cardiac mechanical activity and achieve a greater cardiac output.

In another embodiment, the sensor functions of the invention are utilized to determine the vector of left ventricular ejection and to synchronize the force of chest compression spatially. This might be done utilizing as array of Doppler probes placed over the chest so as to detect the velocity of residual myocardial motion from multiple locations and calculate the vector of that motion.

The vector of left ventricular blood flow ejection is generally from the point of maximal impulse in the left lateral chest between 4th and 6th intercostal spaces near the lateral clavicular line toward the medial cephalad direction. The invention could determine this vector and align the force of chest compression so as to assist ejection of blood and minimize interference with ventricular filling.

Utilizing an indicator of cardiac output, such as exhaled end-tidal carbon dioxide or vital organ oxymetry, the controller circuit could apply synchronized therapies during progressive shock and determine if they benefit the patient through increased blood flow.

DETAILED DESCRIPTION OF THE INVENTION

In a broad sense, the invention relates to techniques and devices that may be used to increase cardiac output for patients suffering from a wide variety of ailments ranging from shock to pulseless electrical activity (PEA) where the patient appears to be lifeless yet has some residual mechanical heart activity. One exemplary technique of the invention is to sense when the heart is beating and then synchronize chest compressions, or other resuscitative techniques, with movement of the myocardial wall. In this way, various techniques may be used to optimally synchronize chest compressions (or other elements of CPR) with residual left ventricular function to improve the outcome of such patients. Hence, the invention may be used to synchronize the compression force of external devices, on or around the chest, with the ejection phase of the residual left ventricular function, and the relaxation phase with residual cardiac filling. In another aspect, the invention provides various techniques and devices for sensing residual mechanical function, and then turn this information into a useful data stream that may be used to operate the various components of resuscitative technology, including adjuncts to blood flow, ventilation, and cardiac stimulating technology.

Such techniques may be used with patients suffering from a wide range of ailments. One exemplary use is for patients who are believed to be in cardiac arrest with pulseless electrical activity (PEA) and non-detectable blood pressures, but who still have residual left ventricular function to some degree. However, it will be appreciated that the invention is not intended to be limited to only such a use, but to a wide range of conditions where there is some organized electrical (but impaired) mechanical cardiac activity.

For example, at one end of such a spectrum is normal spontaneous circulation, where the cardiac outputs are normal and left ventricular mechanical and pumping function are normal. Below that level is compensated shock. In such cases, the blood pressure and the patient's pulse are still palpable and there may be good cardiac output. However, for various reasons, the cardiac output is unable to meet the metabolic demands of the body and homeostasis is at risk. This is evident by parameters such as decreasing urine output and increasing serum lactate, which are markers of inadequate organ function.

Below compensated shock is the state of uncompensated shock. This is a state in which the myocardium and the cardiovascular system is no longer able to provide adequate amounts of blood, oxygen and nutrients to meet the needs of vital organs, and the function of those organs is affected to the extent that they are beginning to become damaged. Blood pressures in this state might be, for example, 70/30 mm Hg. Systolic over diastolic. Also, urine output may cease, and the patient may become confused because of inadequate cerebral function. Importantly, as shock progresses, the pathways to multi-organ system failure are initiated.

Below classical uncompensated shock is what might be called "extreme shock" which borders on cardiac arrest. In this case, the patient exhibits some residual myocardial function including some left ventricular ejection, but cardiac output is wholly inadequate the needs of vital organs. For example, cardiac output might be less than 1 liter per minute, blood pressure might be 50/20, urine output may be minimal or absent, and the patient may be stuporous or comatose. Further, the patient may appear to be near death with significantly impaired cerebral function and stupor bordering on coma. If untreated, extreme shock will result in true cardiac arrest in a timeframe of minutes. Generally, it is not possible to palpate arterial pulses manually in this range, and such patients may be classified as PEA by clinical personnel even thought their heart continues to beat.

Below the state of extreme shock is pulseless electrical activity (PEA) cardiac arrest, which importantly also has a spectrum of conditions and a range of hemodynamics. For example, at its upper end, PEA has both left ventricular mechanical function and cardiac output, but not sufficient enough to be detected as a peripheral radial or femoral pulse. If an intra-arterial catheter is placed into the patient, the blood pressure might be only 45/25, with blood pressure measurable only in major arteries of the chest, neck or groin. A Doppler probe placed over the neck or groin may detect forward blood flow. Blood flow is so profoundly inadequate that the patient will generally appear lifeless and their pupils may dilate and become fixed. Further, they appear to be in cardiac arrest despite the presence of residual pump function and forward flow. The high end of PEA dynamics overlaps the low end of "extreme shock." In such cases, the clinical personnel may not be able to distinguish the differences. The electrocardiogram, while showing organized electrical activity, is variable in its pathology and may be relatively normal in its QRS configuration. The inventor has termed electromechanical dissociation (EMD) with residual myocardial mechanical activity "pseudo-EMD."

Below the "high end" stage of PEA is electromechanical dissociation with almost absent left ventricular function. The blood pressure measured by intravascular catheters just above the aortic valve will show aortic pulsations but the blood pressures measured are on the order of 25/15 mm HG, and there will be almost no associated forward blood flow. Without application of CPR, oxygen delivered to the vital organs will be close to 0 and irreparable injury to organs such as the brain occurs within minutes. The electrocardiogram rarely has a normal appearing QRS configuration, and the overall pattern of the ECG may be slurred out and irregular.

The final stage of PEA is an organized electrical rhythm but no left ventricular mechanical function. This is true cardiac arrest. A catheter measuring pressures above the aortic valve will detect no pressure pulse And echocardiography will show no movement. Further, the cardiac output is 0 and the patient is in complete global ischemia and cardiac arrest. Without application of CPR, oxygen delivered to the vital organs will be 0, and irreparable injury to organs such as the brain occurs within minutes. The overall pattern of the ECG is invariably slurred out and irregular.

Along the spectrum described above, the invention may be used in all cases where there is some myocardial mechanical activity and synchronization resuscitative therapies may improve cardiac output. In such cases, the invention may be used to detect residual mechanical activity and to synchronize such activity of the heart with resuscitation techniques, such as those used in CPR (including chest compressions/decompressions and/or ventilation). Hence, the invention may be utilized in any pathophysiologic state from true cardiac arrest, to pseudo-EMD PEA through the various stages of shock, in any hemodynamics state in which residual myocardial mechanical function with and without cardiac output exists. By synchronizing chest compressions and/or decompressions, among other potentially cyclical therapies, both ejection and filling phases of the cardiac cycle may be augmented. In so doing, cardiac output and organ profusion may be increased, thereby improving the outcome of patients with impaired hemodynamics.

As one particularly important example, one clinical situation that often occurs and is challenging for physicians, is when patients progress from shock to PEA cardiac arrest. In the earlier stages of this process, physicians tend to treat such patients with intravenous medications and possibly controlled ventilation. While drugs such as antibiotics may be administered to patients in states such as septic shock, pressor drugs such as dopamine continue to be a mainstay of treatment. Pressors, however, have generally not been shown to improve the outcome of such patients despite raising the blood pressure. This may be because they improve blood pressure but also raise vital organ oxygen utilization, such that the overall balance between oxygen supply and demand is not improved. Pressor drugs also have significant direct vital organ toxicity.

If, however, these parenteral therapies do not stabilize the patient, their shock may progress inexorably towards more and more extreme states and eventually become cardiac arrest. Many practitioners in emergency medicine and critical care continue to be unsure—and the medical literature remains unclear—as to which point a patient whose blood pressure is dropping should begin to receive chest compressions. Indeed, physicians generally do not apply techniques such as external chest compress before subjective loss of vital signs. This is because CPR, and in particular chest compressions, can interfere with cardiac function and in particular cardiac filling if applied in an unsynchronized manner. For instance, a patient whose blood pressure is 60/40 who begins to receive chest compressions out of synchronization with heart function could rapidly progress into full cardiac arrest. More specifically, in performing CPR without synchronization, application of the compression phase when the left ventricle is trying to fill may significantly decrease cardiac output on the next ejection secondary to the Frank Starling Law of the heart. Hence, by detecting myocardial mechanical function, chest compressions can be synchronized with the ejection phase so that patients in shock may be treated without exacerbating their condition and possibly moving them toward cardiac arrest.

Hence, according to the invention, the issue as to when chest compressions should begin when a patient is progressing through the stages of shock may be addressed by synchronizing chest compressions, and possibly other mechanical adjuncts, with the ejection and relaxation phases so that the clinician may be more confident that chest compressions are assisting and not interfering with residual circulatory function. In this way, the clinician does not need to be as concerned with the question as to when to begin chest compressions. In this manner, the invention may act to allow use of external mechanical adjuncts in the treatment of any form of shock in a manner similar to the methods by which intra-aortic balloon counterpulsation has been applied in cardiogenic shock. The invention may thus allow application of such adjuncts in the pre-hospital, and Emergency Department environments.

Another advantage of using synchronization is that it may be performed as a adjunct to therapies directed at the cause of the shock, such as antibiotics or thrombolysis, enhancing vital organ perfusion while these therapies are being administered. Indeed, improved hemodynamics may not only stave off organ injury, it may improve the efficacy of parenteral therapies. Further, synchronized chest compressions are unlikely to have significant organ toxicity, unlike pressor drugs.

As described above, one particular application of the invention is in connection with those suffering from pulseless electrical activity (PEA). PEA is one of the three broad-types of cardiac arrest, the other two being ventricular fibrillation and asystole. PEA is also referred to as electromechanical disassociation (EMD). PEA has been described as "the presence of organized electrical activity on the electrocardiogram but without palpable pulses." Rosen P, Baker F J, Barkin R M, Braen G R, Dailey R H, Levy R C. Emergency Medicine Concepts and Clinical Practice. 2nd ed. St Louis: CV Mosby, 1988. Unlike ventricular fibrillation, which can be specifically reversed with electrical countershock, PEA does not have a specific countermeasure. This may explain the traditionally worse outcome of patients in PEA compared to ventricular fibrillation. Unfortunately, the incidence of PEA is increasing, possible because early risk modification is changing the natural history of cardiovascular disease. It is now reported by some authorities that the majority of patients in cardiac arrest are in PEA at the time of EMS arrival. Additionally, a significant fraction of patients that are shocked out of ventricular fibrillation, or resuscitated from asystole, will experience PEA at some point during their resuscitation. The combination of these circumstances mean that a large majority of patients receiving advanced life support for treatment of cardiac arrest will have PEA at some time during resuscitation. Hence, now or in the near future PEA may supersede classical ventricular fibrillation in importance. It may already have done so.

One important feature of the invention is the discovery that many patients with PEA have residual cardiac mechanical activity, and many have detectable blood pressures. This condition may be referred to as pseudo-EMD PEA. In such cases, the patient may appear lifeless and without a pulse. However, there often remains some degree of residual left ventricular function. Hence, one important feature of the invention is to sense when the patient still has some myocardial function and then to synchronize phasic resuscitation therapies, especially compression of the chest, with the heart's residual mechanical function. In this way, the compression phase of CPR may occur during the ejection phase, and the relaxation phase can allow elastic recoil of the chest—with associated decreases in intrathoracic pressure when the left ventricle is trying to fill. In this way, synchronizing phasic resuscitative therapies with residual ventricular ejection and filling, may improve hemodynamics, the rate of ROSC, and long term survival.

The invention may incorporate various non-invasive sensing technologies to acquire real-time data describing the pattern of myocardial wall and or valve motion so as to allow synchronization of chest compressions and other therapies. If, however, invasive indicators of hemodynamics, such as intra-arterial pressure or flow monitors, are present, then the invention may act as an interface between those inputs and phasic resuscitative therapies as exemplifies by external chest compression. To apply proper synchronization between the forces of external devices, on or around the chest or body, and the ejection and filling phases of residual left ventricular function, a variety of devices may be used. The decision that residual myocardial activity exists may be made from a logic circuit with inputs from multiple sensing modalities. The invention may utilize sensing technology to collect the data on myocardial wall function, myocardial valve motion, blood flow in vascular structures, vital organ oxygen or energy status, or exhaled pulmonary gas, and this data may be passed through logic circuits and an controlling output signal passed to the devices that deliver therapies. Because the pattern of mechanical residual wall function may be variable over time, the invention may be designed to promptly identify residual function and to vary therapeutics based on feed back to a logic circuit. Also, the synchronizing of external chest compressions may be used with other techniques, such as with abdominal counter pulsations, phasic limb compression, ventilation, and electrical stimulation, among others, to augment cardiac ejection and filling. In this way, the patient may be stabilized to allow sufficient time for primary therapies, such as thrombolysis, to be effective.

A wide variety of equipment and device may be used to provide chest compressions. For example, various types of automated compression systems may be use to compress the chest. These include systems, such as the Auto Pulse Resuscitation System, by Revivant of Sunnyvale, Calif., the Thumper manufactured by Michigan Instruments or the LUCAS device for automated active compression, and the like. Further, the invention is not limited to automated compression systems, but may be used with manual techniques as well. For example, the invention may be used to provide an audio and/or visual signal to indicate to a rescuer as to when to manually apply chest compressions. Further, in some cases a suction device may be adhered to the chest so that the chest may be actively lifted intermittently with chest compressions.

Using either manual or automated equipment, the invention may be configured to synchronize external chest compressions with any residual mechanical activity of the myocardium such that when the myocardium enters pumping or systole phase, CPR is in the compression phase. Further, when the heart enters its refilling or diastole phase, chest compressions enter the relaxation phase. Sensory efficacy data may be passed through a logic circuit and outputs of that circuit used to control the intervals of cardiac ejection or filling that optimize the effect of synchronization.

In addition to synchronizing chest compressions with residual heart function, the invention may also be use to synchronize ventilations with residual heart function. For example, inspiration and expiration may be synchronized with residual myocardial function so as to optimize the increase in cardiac output. For instance, inspiration may be synchronized to systole and expiration with diastole. To apply ventilations, the invention may use a traditional ventilator or ventilations may be provided manually, such as by using a ventilatory bag. In the latter case, an audio and/or visual signal may be provided to the rescuer as to when to apply proper ventilations.

With both chest compressions and ventilations, the timing, frequency and/or duration may be varied depending on the particular treatment. For example, chest compressions may occur during the entire systole phase, or only during a portion of it. Further, chest compressions may occur every systole phase or during only certain systole phases. A similar scenario may occur with ventilations. The controller may use one or more sensory inputs, and a logic circuit utilizing and indicator or indicators of efficacy, to optimize the effect of synchronization on hemodynamics.

The invention may be utilized with any therapy that may benefit from synchronization with residual myocardial mechanical function in apparently lifeless patients. Chest compression and decompression, abdominal counter-pulsation, ventilation, phasic limb-compression, myocardial electrical stimulation, intravascular fluid shifting, intravascular or intra-pericardial balloon inflation-deflation, application of transthoracic electromagnetic irradiation, among others. The controller logic circuit may vary the pattern of synchronization among multiple therapies so as to determine the optimal pattern with respect to increasing hemodynamics.

To sense myocardial wall function, a variety of noninvasive devices and technologies may be used. For example, one technology that may be used is electrocardiography (ECG). ECG may be an attractive detection method because it is already used in most clinical situations during resuscitation. However, because myocardial activity is not always present with ECG during PEA, it may need to be used in combination with other sensing techniques as described below. Another example of a sensing technique that may be used is Doppler ultrasonography (DOP). Doppler ultrasound uses the Doppler shift of ultrasonic wave to quantify the blood flow in peripheral vessels. This may be applied with a transducer on the neck for carotid flow, the groin for femoral flow, or a transthoracic or intraesophageal transducer for aortic flow. A Doppler probe may also be placed at the cardiac point of maximum impulse to detect movement of blood within the myocardium. An array of Doppler probes may be used to determine the vector of residual myocardial mechanical function and align chest compression and relation with that vector.

A further sensing technique that may be used is plethysmography (PLETH). Plethysmography may be applied by measuring changes in the transthoracic AC electrical impedance with heart motion. A further technique that may be used is phonocardiography (PHONO). Phonocardiography records the acoustical energy detected by a stethoscope over the heart. Still a further technique that may be used is echocardiography (ECHO). With echocardiography or ultrasound imaging of the heart, left ventricular ejection can be quantified. In some cases, echocardiograph detection of heart function may be combined with ECG. Also, sensitivity may be improved through the use of intravenously injected microbubbles or other ultrasound enhancing technologies.

It may be optimal to combine a number of these detection systems so as to increase the sensitivity and specificity of detecting residual myocardial mechanical function. Additionally, it may be optimal to incorporate a logic circuit which compares combinations of sensing technologies to an indicator of actual cardiac output, such as end-tidal carbon dioxide or aortic flow. In this manner, the invention could determine which combination of sensing technologies are most predictive of improvements derived from synchronization.

Additionally, the logic circuit of the invention might be capable of varying the synchronized therapeutics against indicators of actual cardiac output so as to determine which pattern of synchronized therapy is most effective. It may vary synchronization within one therapeutic device or multiple therapeutic devices so as to identify the optimal pattern.

Figure 1:
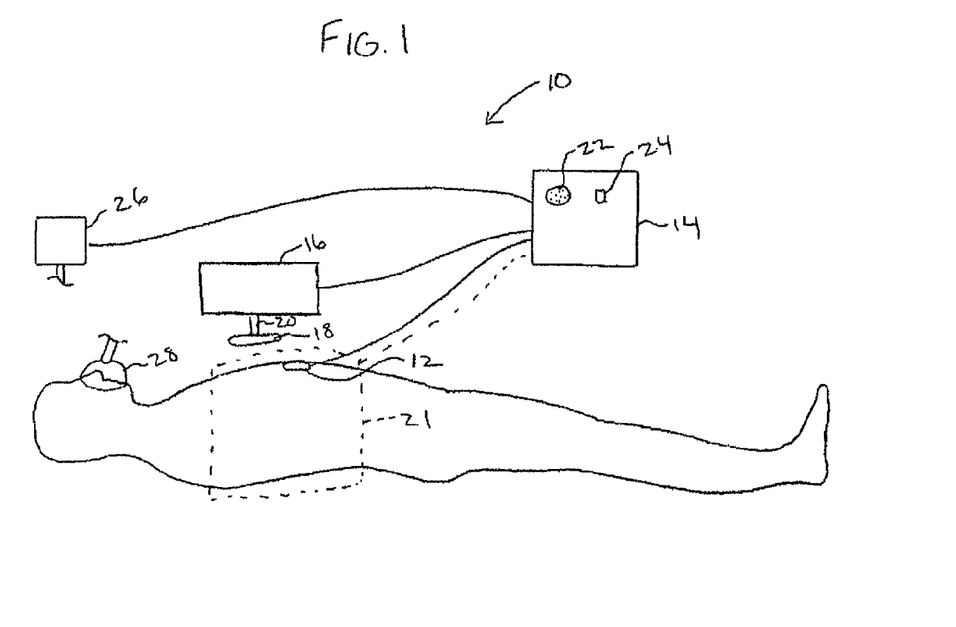
FIG. 1 is a is a schematic view of a system that may be used to improve the cardiac output of a patient according to the invention.

Referring now to FIG. 1, a system 10 for improving cardiac output will be described. System 10 includes a sensor, or sensors, 12 that may be used to detect residual myocardial mechanical function. In one embodiment, sensor 12 may comprise a surface probe that rests on the patient's chest. Sensor 12 may be placed at a variety of locations on the chest. For example, one location may be the anterior chest in one of the intercostal spaces. Another location may be the sub-xi-phoid location in the epigastrium. Sensor 12 may sense myocardial wall motion using any of the technologies described herein, including ultrasound, Doppler technology, echocardiography, plethysmography and the like. As an alternative to placing sensor 12 on the patient's chest, it will be appreciated that other locations may be used as well, such as a probe that is placed on the neck over the carotids, or into the patient's esophagus. It will also be appreciated that sensor 12 may be an array of sensors.

The data collected by sensor 12 is transmitted to a controller 14 having signal processing and logic capabilities. A further description of controller 14 will be described hereinafter with reference to FIG. 2. Controller 14 is also electronically coupled to a compression device 16 that may be used to apply external chest compression to the patient. In some embodiments, it will be appreciated that controller 14 could be incorporated into compression device 16 or into any of the sensors. For ease of use, both the sensor 12 and the controller 14 may be incorporated into the therapy device 16. Further, controller 14 could be wirelessly connected to the sensing and/or compression devices. In the example illustrated in FIG. 1, chest compression device 16 includes an interface member 18 that is coupled to a piston 20 which moves interface member 18 against the chest in a repeating manner. In this way, chest compression device 16 may apply repeating chest compressions to the patient. In some cases, interface member 18 may be configured to adhere to the patient's chest so that as piston 20 lifts interface member 18, the patients' chest will also be lifted. In this way, chest compression device 16 may apply alternating chest compressions and decompressions. Although described in the context of chest compression device 16, it will be appreciated that a wide variety of equipment may be used to apply chest, abdomen or extremity compressions and/or decompressions in an automated manner as described herein, and that the invention is not intended to be limited to only the specific embodiment of chest compression device 16. For instance, examples of existing CPR equipment that may be modified to function in connection with controller 14 include the AutoPulse Resuscitation System by Revivant of Sunnyvale, Calif., or the Thumper manufactured by Michigan Instruments. As another option, an inflatable vest 21 may be coupled to controller 14 and be configured to be inflated and deflated to perform proper synchronization.

As an alternative to applying automated chest compressions, the invention may also be used with manual techniques. In such cases, controller 14 may include a speaker 22 and/or a light 24 that provide information to a rescuer as to when to apply chest compressions and/or decompressions. For example, speaker 22 may be configured as a metronome to apply a repeating signal, or could give instructions in a human understandable voice. Light 24 may be configured to repeatedly flash to indicate when to apply chest compressions and/or decompressions. It will also be appreciated that a force transducer may be placed between the hands of the person providing manual chest compression and the patients such that the force, timing and vector of chest compression can be sensed so that the accuracy of synchronization is evaluated.

Chest compressions may be applied at a variety of locations. Examples include the sternal area, parasternal areas, circumferentially, the back, and the like. The abdomen may be compressed or counterpulsed broadly or with specific emphasis on the areas of the abdominal aorta or inferior vena cava. The extremities may be compressed rhythmically. The pattern of ventilation may be varied.

Controller 14 configured to receive data from sensor 12 and then process the signals in order to operate chest compression device 16, speaker 22 or light 24. More specifically, controller 14 is configured to synchronize external chest compressions and/or decompressions with any residual mechanical activity of the myocardium sensed by sensor 12. In this way, when the myocardium enters the pumping or systole phase, chest compression device 16 is configured to force interface member 18 against the chest to apply a chest compression. When the heart enters its refilling or diastole phase, controller 14 is configured to lift interface member 18 so that no compressive forces are being applied to the chest. It is understood that the therapeutic impulses may be restricted to a portion of each phase.

System 10 further includes a ventilation system 26 that is coupled to controller 14. For example, ventilation system 26 may comprise a ventilator that is in fluid communication with a mask 28. Controller 14 may be configured to synchronize inspiration and expiration to residual myocardial function as detected by sensor 12. For example, ventilation system 26 may be configured to provide positive pressure ventilations during systole and allow for expiration during diastole, or vice versa. Controller 14 may also be configured to coordinate operation of ventilation system 26 with chest compression device 16. As an option to using a mechanical ventilator, the invention may also utilize other techniques, such as a ventilatory bag that may be mechanically squeezed by the patient. In such cases, speaker 22 or light 24 may be actuated to indicate to the rescuer as to when to apply proper ventilations.

Figure 2:
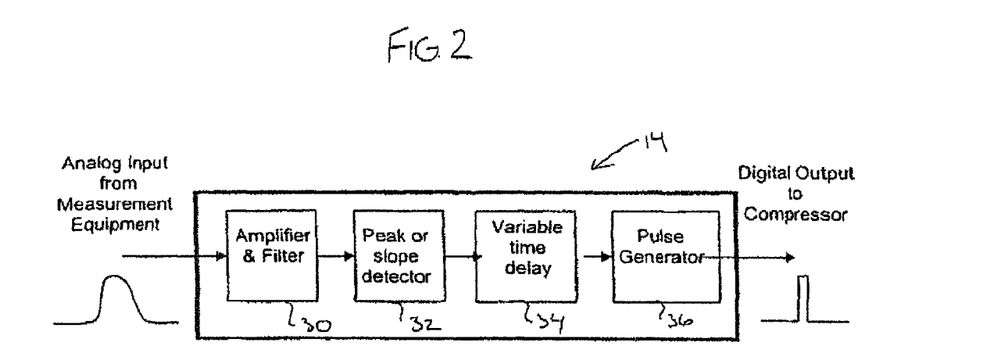
FIG. 2 is a schematic diagram of a controller that may be used to actuate a compression device based on signals from a myocardial activity sensor according to the invention.

Referring now to FIG. 2, one aspect of controller 14 will be described in greater detail. As previously described, controller 14 receives signals from sensor 12 regarding residual myocardial wall function. Typically, signals from sensor 12 will be in analog form. As such, controller 14 may include an amplifier and filter 30 which amplify and filter the analog signal. Controller 14 also includes a peak or slope detector 32 which is circuitry that detects either peaks or slopes of the analog signal that are indicative of myocardial wall motion. Detector 32 may be configured to trigger on rapid increases in signal amplitude. The triggered signal from detector 32 will pass through a variable time delay circuitry which is fed to a pulse generator 36 that converts the analog trigger into a digital pulse of fixed amplitude and duration. The variable time delay 32 may be added to this pulse to allow for fine adjustment of synchronization in timing. The delayed pulse is then processed as an output to chest compression device 16 in digital format.

The controller may combine inputs from a number of sensing systems so as to increase the sensitivity and specificity of detecting residual myocardial mechanical function. Additionally, it may be optimal to incorporate a logic circuit, possibly within a microprocessor, which compares combinations of sensing technologies to an indicator of actual cardiac output, such as end-tidal carbon dioxide or aortic flow. In this manner, the invention could determine which combination of sensing technologies are most predictive of improvements derived from synchronization. Additionally, the logic circuit of the invention might be capable of varying the synchronized therapeutics and comparing the combinations to amount of residual myocardial synchronization and measured cardiac output so as to determine which pattern of synchronized therapy is most effective.

Figure 3:
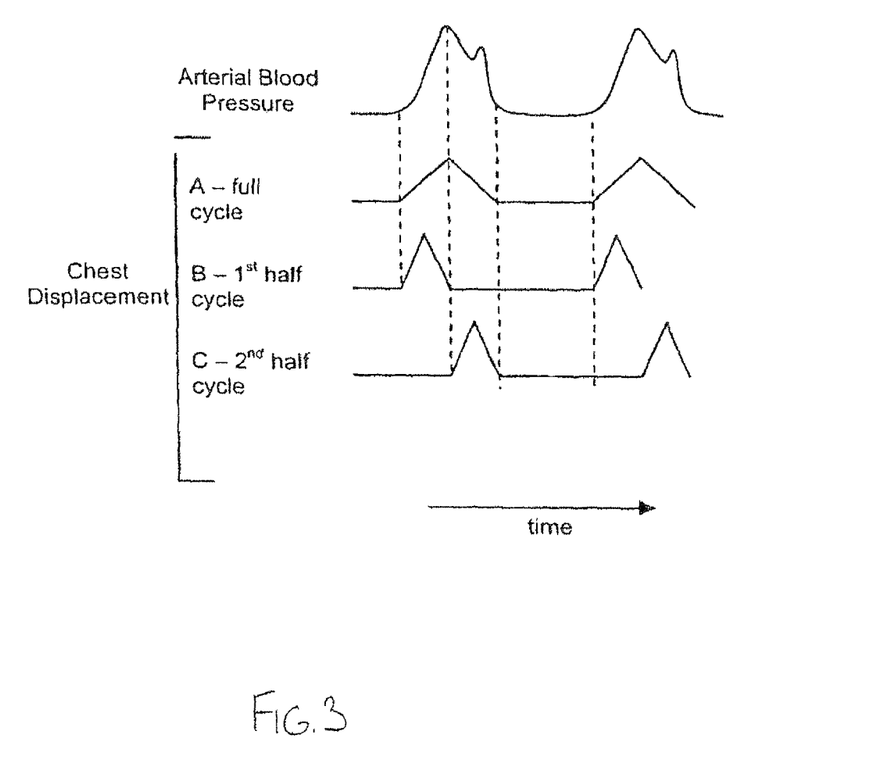
FIG. 3 is a graph illustrating exemplary times for applying compressive forces according to the invention.

As previously mentioned, chest or abdominal compressions and/or ventilations may be applied during different times of the cardiac cycle and may be varied over the cycles themselves. For example, as illustrated in FIG. 3, a chest compression may be applied each time the sensor detects the ejection phase, and this compression may occur throughout the entire ejection phase. Alternatively, the chest compression could be applied only during the first half of the ejection cycle. As another option, the chest compression could be applied during the second half of the ejection cycle. As a further alternative, chest compressions could be applied during each ejection cycle, or only during certain ejection cycles, such as every second, third, or fourth ejection cycle. Also, the magnitude of chest compressions may be evaluated to determine if they should be increased or decreased throughout the procedure. A similar scenario may be used for chest decompressions, abdominal compression decompression or counterpulsations, limb compressions, and the phases of ventilations.

In summary, by utilizing a sensor, or combination of sensors, an apparently lifeless patient's residual myocardial wall function may be detected and the application of phasic resuscitative therapies, including chest compressions and/or decompressions as well as abdominal counterpulsations, and ventilations may be precisely controlled so that the application of CPR components enhances, and does not interfere with the existing mechanical activity of the heart. The device may also potentially be used in patients suffering severe shock with residual signs of life.

Figure 4:
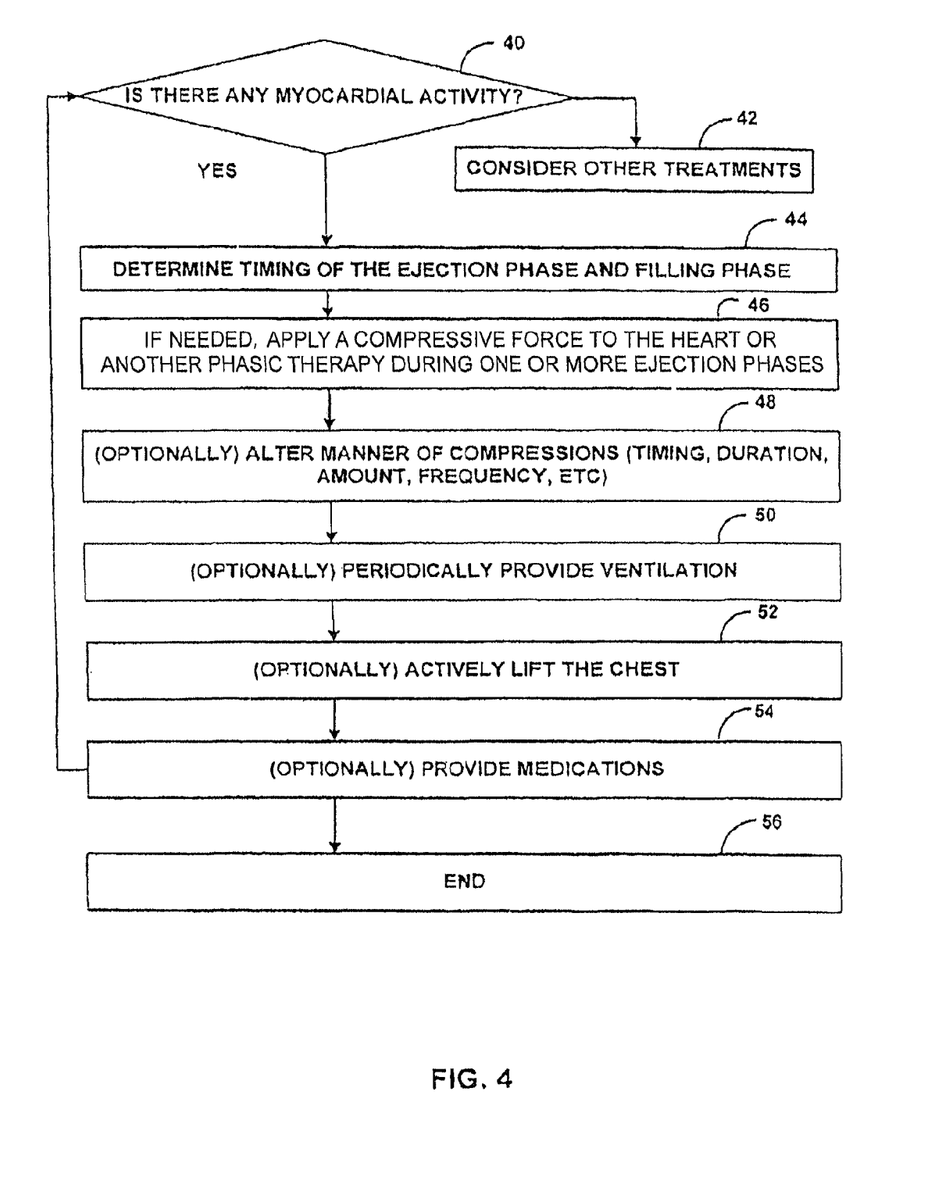
FIG. 4 is a flow chart illustrating one method for improving the cardiac output of a patient according to the invention.

Referring now to FIG. 4, one exemplary method for treating a patient suffering from ailments ranging from shock to PEA will be described. Initially, the patient is evaluated to determine if there is any myocardial activity as illustrated in step 40. If myocardial activity is not present, the rescuer may wish to consider other treatments as illustrated in step 42. For example, such treatments could include the use of a defibrillating shock as is known in the art. If some myocardial wall activity is detected, the process proceeds to step 44 where the timing of the ejection phase and filling phase is determined. As previously described, this may be determined by the use of a sensor that is used to sense myocardial wall activity. Also determined may be the vector and baseline oxygen or energy state of vital organs. Depending on the amount of activity exhibited by the heart, a compressive force or another phasic therapy may be applied to the heart during one or more of the ejection phases as illustrated in step 46. This may be accomplished by using automated equipment or by using manual techniques. In either event, the applied compressive forces may be synchronized with the ejection phase so that the compressive forces do not interfere with the refilling phase. Optionally, as illustrated in step 48, the manner of compressions may be varied. This may include the time, duration, amount, frequency, vector, and the like. These variables may be initially set after measuring the amount of myocardial wall activity and may be changed or varied throughout the procedure depending on the patient's physiological condition.

As illustrated in step 50, the patient may periodically be provided with ventilations. The phases of ventilations may also be synchronized with the sensed ejection phases and refilling phases as measured in step 44. Further, the ventilations may be coordinated with the application of the chest compressions.

In some cases, the patient's chest may be actively lifted in an alternating manner with chest compressions as illustrated in step 52. In such cases, the chest may be lifted during the filling phase as measured in step 44.

As another optional step, the patient may periodically be provided with medications as part of the treatment. Examples of medications that may be applied include epinephrine, vasopressin, amiodarone, and the like. Alternative phasic therapies for use in step 46 may also be synchronized with residual myocardial activity. These other phasic therapies may include, among others: abdominal counterpulsation, ventilation, phasic limb-compression, myocardial electrical stimulation, intravascular fluid shifting, intravascular balloon inflation-deflation, application of transthoracic electromagnetic irradiation.

Throughout the procedure, the patient's heart may be continually monitored to determine myocardial activity as well as other physiological conditions. Depending on the patient's condition, any of the items discussed in steps 44-54 may be varied or stopped over time. At step 56, the process ends.

The invention has now been described in detail for purposes of clarity and understanding. However, it will be appreciated that certain changes and modifications may be practiced within the scope of the appended claims.

What is claimed is:

1. A method to treat a patient in shock comprising:
    determining the patient is in a pulseless electrical activity (PEA) condition;
    during the PEA condition, sensing actual residual myocardial motion or residual pulsatile blood flow in the patient using one or more sensors for any of echocardiography, Doppler ultrasonography, plethysmography and phonocardiography,
    determining whether actual myocardial motion or residual pulsatile blood flow is occurring in the patient during the PEA condition, and
    in response to the determination that the actual myocardial motion or residual pulsatile blood flow is occurring, repeatedly applying a phasic therapy to the patient synchronized to the sensed actual myocardial motion or pulsatile blood flow, wherein the phasic therapy includes applying a compressive force to the chest of the patient during at least a portion of an ejection phase of the heart and ceasing the application of the compressive force during at least a portion of a relaxation phase of the heart.

2. A method as in claim 1 wherein the repeated application of the phasic therapy augments cardiac ejection of blood and the cessation of the application of the compressive force avoids interfering with filling of the heart.

3. A method as in claim 1 wherein the phasic therapy includes a second phasic therapy selected from a group consisting of active chest decompression, abdominal compression, ventilation, phasic limb-compression, myocardial electrical stimulation, intravascular fluid shifting, intravascular or internal visceral balloon inflation-deflation, and application of transthoracic electromagnetic irradiation.

4. A method as in claim 1 wherein the compressive force is applied to at least one of a sternal, a parasternal or an intercostal area of the chest.

5. A method as in claim 1 wherein the compressive force is applied during each ejection phase of the heart in which the phasic therapy is applied.

6. A method as in claim 1 wherein the compressive force is applied during less than all of the ejection phase of the heart during a period in which the phasic therapy is applied.

7. A method as in claim 1 wherein the compressive force is applied during a predetermined portion of the ejection phase and the cessation occurs during another portion of the ejection phase.

8. A method as in claim 1 wherein the phasic therapy comprises actively lifting or actively decompressing of the chest during the relaxation phase and during the cessation of the compressive force.

9. A method as in claim 8 wherein the lifting or decompression is applied during an entirety of the relaxation phase.

10. A method of claim 8 wherein the lifting or decompression is applied during a predetermined portion of the relaxation phase and is not applied during another portion of the relaxation phase.

11. A method as in claim 1 further comprising applying or altering ventilations, gas flow or airway pressure of the patient based on the sensed actual myocardial motion or pulsatile blood flow.

12. A method as in claim 1 wherein the compressive force is applied using equipment selected from a group consisting of mechanical compression devices; inflatable vests, nerve or muscle stimulators; and a suction based compression-decompression device.

13. A method as in claim 1 wherein a sensing system senses the actual myocardial motion or pulsatile blood flow.

14. A method as in claim 13 wherein the sensing system comprises an array of sensors applied to the patient.

15. A method as in claim 1 further comprising displaying or broadcasting information indicating the sensed actual myocardial motion or pulsatile blood flow.

16. A method as in claim 15 wherein the repeated application of the phasic therapy is applied manually in synchronization with the displayed or broadcasted information.

17. A method as in claim 1 further comprising a determination that the patient is suffering from shock before the repeated application of the phasic therapy.

18. A method to treat a patient as in claim 1 further comprising determining the patient is suffering pulseless electrical activity (PEA).

19. A method to treat a patient comprising:
determining the patient is in a pulseless electrical activity (PEA) condition;
during the PEA condition, sensing actual residual myocardial motion or residual pulsatile blood flow in the patient using one or more sensors for any of echocardiography, Doppler ultrasonography, plethysmography and phonocardiography,
determining whether actual myocardial motion or residual pulsatile blood flow is occurring in the patient during the PEA condition, and
in response to the determination that the actual myocardial motion or residual pulsatile blood flow is occurring, repeatedly applying a phasic therapy to the patient synchronized to the sensed actual myocardial motion or pulsatile blood flow, wherein the phasic therapy includes applying a compressive force to the chest of the patient during an ejection phase of the heart of the patient and ceasing the application of the compressive force during a relaxation phase of the heart.

20. A method to treat a patient as in claim 19 further comprising determining the patient is in shock before the repeated application of the phasic therapy.

21. A method to treat a patient as in claim 19 further comprising determining the patient is suffering pulseless electrical activity (PEA) before applying the phasic therapy.

22. A method to treat a patient as in claim 19 further comprising determining the patient is suffering cardiac arrest before the repeated application of the phasic therapy.

23. A method as in claim 19 wherein the repeated application of the phasic therapy augments cardiac ejection of blood and the cessation of the application of the compressive force avoids interfering with filling of the heart.

24. A method as in claim 19 wherein the phasic therapy includes a second phasic therapy selected from a group consisting of active chest decompression, abdominal compression, ventilation, phasic limb-compression, myocardial electrical stimulation, intravascular fluid shifting, intravascular or internal visceral balloon inflation-deflation, and application of transthoracic electromagnetic irradiation.

25. A method as in claim 19 wherein the compressive force is applied to at least one of a sternal, a parasternal or an intercostal area of the chest.

26. A method as in claim 19 wherein the compressive force is applied during each ejection phase of the heart in which the phasic therapy is applied.

27. A method as in claim 19 wherein the compressive force is applied during less than all of the ejection phase of the heart during a period in which the phasic therapy is applied.

28. A method as in claim 19 wherein the compressive force is applied during a predetermined portion of the ejection phase and the cessation occurs during another portion of the ejection phase.

29. A method as in claim 19 wherein the phasic therapy comprises actively lifting or actively decompressing of the chest during the relaxation phase and during the cessation of the compressive force.

30. A method as in claim 29 wherein the lifting or decompression is applied during an entirety of the relaxation phase.

31. A method of claim 29 wherein the lifting or decompression is applied during a predetermined portion of the relaxation phase and is not applied during another portion of the relaxation phase.

32. A method as in claim 19 further comprising applying or altering ventilations, gas flow or airway pressure of the patient based on the sensed actual myocardial motion or pulsatile blood flow.

33. A method as in claim 19 wherein the compressive force is applied using equipment selected from a group consisting of mechanical compression devices; inflatable vests, nerve or muscle stimulators; and a suction based compression-decompression device.

34. A method as in claim 19 wherein a sensing system comprises an array of sensors applied to the patient and the sensing system performs the sensing of the actual residual myocardial motion or the residual pulsatile blood flow.

35. A method as in claim 19 further comprising displaying or broadcasting information indicating the sensed actual myocardial motion or pulsatile blood flow.

36. A method as in claim 35 wherein the repeated application of the phasic therapy is applied manually in synchronization with the displayed or broadcasted information.

37. A method to treat a patient who is suffering from pulseless electrical activity, shock or other ailment of the heart, the method comprising:
determining the patient is in a pulseless electrical activity (PEA) condition;
during the PEA condition, sensing residual myocardial activity to determine left ventricular pump function or blood filling or ejection using one or more sensors for any of echocardiography, Doppler ultrasonography, plethysmography and phonocardiography;
determining whether actual myocardial motion or residual pulsatile blood flow is occurring in the patient during the PEA condition;
characterizing at least one of a pattern, a timing, a force and a vector of the sensed left ventricular pump function, or blood filling or ejection;
in response to the determination that the actual myocardial motion or residual pulsatile blood flow is occurring, repeatedly applying a phasic therapy to the patient, and
synchronizing the phasic therapy with the characterized at least one of the pattern, the timing, the force and the vector of the determined left ventricular pump function or blood filling or ejection.

38. A method as in claim 37 wherein the synchronization of the phasic therapy augments cardiac ejection and minimizes interfering with cardiac filling.

39. A method as in claim 37 wherein the phasic therapy is applied at a location on the patient based on at least one of the pattern, the timing, the force or the vector of the left ventricular pump function or blood filling or ejection.

40. A method as in claim 37 wherein the characterization of at least one of a pattern, timing, force and vector of the determined left ventricular pump function includes determining occurrences of ejection phases of the heart of the patient, and the phasic therapy comprises repeating chest compressions and the synchronization of the phasic therapy includes applying the chest compressions during at least some ejection phases.

41. A method as in claim 40 wherein the compressive force is applied during each determined ejection phase.

42. A method as in claim 40 wherein the compressive force is applied selectively during some but not all of the determined ejection phases.

43. A method of claim 37 wherein the characterization of at least one of the pattern, the timing, the force and the vector of the determined left ventricular pump function includes determining occurrences of relaxation phases of the heart of the patient, and the synchronization of the phasic therapy includes ceasing the chest compressions during the relaxation phases.

44. A method as in claim 37 wherein the phasic therapy includes a plurality of phasic therapies applied to the patient and the phasic therapies include two or more of a group consisting of chest compressions, abdominal counter-pulsation, ventilation, phasic limb-compression, myocardial electrical stimulation, intravascular fluid shifting, intravascular or internal visceral balloon inflation-deflation, and application of transthoracic electromagnetic irradiation.

45. A method as in claim 44 wherein the compressive force is applied to the sternal, parasternal or intercostal areas of the chest.

46. A method as in claim 44 further comprising sensing actual cardiac output and varying the application of the phasic therapies based on the sensed actual cardiac output.

47. A method as in claim 46 wherein the sensed actual cardiac output is represented by a surrogate of hemodynamics.

48. A method as in claim 47 wherein the hemodynamics is at least one of end-tidal carbon dioxide and sensed arterial flow.

49. A method as in claim 46 the variation of the application of the phasic therapies increases the sensed cardiac output.

50. A method as in claim 37 wherein the sensing includes data collected from an array of Doppler probes placed over the chest, neck or abdomen and from data determining a velocity or magnitude of residual myocardial motion or surrogate hemodynamics.

51. A method as in claim 50 wherein the data is collected from multiple probe locations on the chest, neck or abdomen, and the determination of the velocity or magnitude includes calculation of a vector of the residual myocardial motion or blood filling or ejection.

52. A method to treat a patient comprising:
    determining the patient is in a pulseless electrical activity (PEA) condition;
    during the PEA condition, sensing residual myocardial activity of a heart of the patient or residual pulsatile blood flow pumped by the heart using one or more sensors for any of echocardiography, Doppler ultrasonography, plethysmography and phonocardiography;
    determining that actual myocardial motion or residual pulsatile blood flow is occurring based on the sensing;
    in response to the determination that there is actual myocardial motion or residual pulsatile blood flow, repeatedly applying a phasic therapy to the patient in synchronization with the sensed myocardial activity;
    sensing actual cardiac output or a surrogate of actual cardiac output, and
    varying the application of the phasic therapy based on the sensed actual cardiac output or the surrogate.

53. A method as in claim 52 wherein the sensing of the myocardial activity is applied to determine a left ventricular pump function, a mechanical activity of blood filling or ejection of the heart.

54. A method as in claim 52 wherein the repeated application of the phasic therapy augments cardiac ejection of blood.

55. A method as in claim 52 wherein the phasic therapy includes a second phasic therapy selected from a group consisting of active chest decompression, abdominal compression, ventilation, phasic limb-compression, myocardial electrical stimulation, intravascular fluid shifting, intravascular or internal visceral balloon inflation-deflation, and application of transthoracic electromagnetic irradiation.

56. A method as in claim 52 wherein the phasic therapy includes a compressive force applied to at least one of a sternal, a parasternal or an intercostal area of the chest.

57. A method as in claim 56 wherein the compressive force is applied during each ejection phase of the heart in which the phasic therapy is applied.

58. A method as in claim 56 wherein the compressive force is applied during less than all of the ejection phase of the heart during a period in which the phasic therapy is applied.

59. A method as in claim 56 wherein the compressive force is applied during a predetermined portion of the ejection phase and the cessation occurs during another portion of the ejection phase.

60. A method as in claim 52 wherein the phasic therapy comprises actively lifting or actively decompressing of the chest during the relaxation phase and during the cessation of the compressive force.

61. A method as in claim 60 wherein the lifting or decompression is applied during an entirety of the relaxation phase.

62. A method of claim 60 wherein the lifting or decompression is applied during a predetermined portion of the relaxation phase and is not applied during another portion of the relaxation phase.

63. A method as in claim 52 further comprising applying or altering ventilations, gas flow or airway pressure of the patient based on the sensed actual myocardial motion or pulsatile blood flow.

64. A method as in claim 56 wherein the compressive force is applied using equipment selected from a group consisting of mechanical compression devices; inflatable vests, nerve or muscle stimulators; and a suction based compression-decompression device.

65. A method as in claim 52 wherein the sensing comprises sensing with an array of the sensors applied to the patient.

66. A method as in claim 52 further comprising displaying or broadcasting information indicating the sensed actual myocardial motion or the sensed surrogate.

67. A method as in claim 66 wherein the repeated application of the phasic therapy is applied manually in synchronization with the displayed or broadcasted information.

68. A method as in claim 52 further comprising a determination that the patient is suffering from shock before the repeated application of the phasic therapy.

69. A method to treat a patient as in claim 52 further comprising determining the patient is suffering pulseless electrical activity (PEA).

70. A method as in claim 52 further comprising varying the application of the phasic therapy to cause an increase in the sensed indicator of cardiac output.

71. A method as in claim 70 wherein the variation in the application of the phasic therapy or phasic therapies includes varying at least one of a pattern, a timing, a force, and the vector, of a compressive force applied to the patient in synchronization with the sensed myocardial activity.

72. A method as in claim 56 wherein the compressive force is applied to the patient's chest at the sternal or parasternal, or left intercostal areas, and the variation in the application includes changing the location on the chest where the compressive force is applied.

73. A method as in claim 70 wherein the variation in the application of the phasic therapy includes selecting another phasic therapy to be applied wherein the selected phasic therapy is selected from a group consisting of chest compressions, abdominal counter-pulsation, ventilation, phasic limb-compression, myocardial electrical stimulation, intravascular fluid shifting, intravascular or internal visceral balloon inflation-deflation, and application of transthoracic electromagnetic irradiation.

74. A method as in claim 52 wherein the sensed indicator of actual cardiac output includes at least one of sensed end-tidal carbon dioxide or sensed arterial flow.

75. A method as in claim 70 further comprising generating audible or visual prompts to notify a health care provider when to apply the phasic therapy to the patient, and the variation includes varying a timing of the prompts.

76. A method as in claim 52 further comprising repeatedly ventilating the patient and varying the ventilation, gas flow or airway pressure of the patient based on the sensed actual cardiac output.

77. A method as in claim 76 wherein the ventilation of the patient is synchronized with the application of the sensed myocardial movement.

78. A method to optimize vital heart organ blood flow in a patient having a chest and a heart comprising:

determining the patient is in a pulseless electrical activity (PEA) condition;

during the PEA condition, sensing at least one of actual residual blood flow, an indicator of the actual residual blood flow and a status of a vital organ of the patient and generating blood flow data from the sensing, wherein the sensing uses one or more sensors for any of echocardiography, Doppler ultrasonography, plethysmography and phonocardiography;

based on the determination that the actual myocardial motion or residual pulsatile blood flow is occurring, repeatedly applying a compressive force to the chest of the patient in synchronization with the blood flow data, and     adjusting further application of the compressive force based on current values of the blood flow data sensed after the repeated application of the compressive force.

79. A method for improving the cardiac output of a patient, the method comprising:

determining the patient is in a pulseless electrical activity (PEA) condition;

during the PEA condition, detecting residual myocardial mechanical activity and residual pump function using one or more sensors for any of echocardiography, Doppler ultrasonography, plethysmography and phonocardiography,     determining that actual myocardial motion or residual pulsatile blood flow is occurring based on the sensing;

in response to the determination that there is actual myocardial motion or residual pulsatile blood flow, repeatedly applying a compressive or a decompressive force to the chest at least during a portion of an ejection phase of the heart and ceasing application of the compressive force, or applying the decompressive force during a portion of the relaxation phase, and     adjusting at least one of a start of the application of the compression force, a termination of the compression force and an initiation or termination of the decompressive force.

80. A method as in claim 79 further comprising sensing actual cardiac output or sensing a surrogate indicator of cardiac output, and wherein the adjusting is based on the sensed actual cardiac output or the sensed surrogate indicator.

81. A method as in claim 80 wherein the compressive force is applied to the patient's chest at the sternal or parasternal, or left intercostal areas.

82. A method as in claim 79 wherein the compressive force is applied during each sensed ejection phase.

83. A method as in claim 79 wherein the compressive force is applied only at certain ejection phases.

84. A method as in claim 79 wherein the compressive force is applied for only a certain duration of the ejection phase.

85. A method as in claim 79 wherein the phasic therapy includes actively lifting or active decompression of the patient's chest.

86. A method as in claim 85 wherein the lifting or the active decompression is applied only at certain relaxation phases of the heart or for a certain duration of the relaxation phases.

\* \* \* \* \*